United States Patent
Benstead et al.

(10) Patent No.: US 10,787,412 B2
(45) Date of Patent: *Sep. 29, 2020

(54) RECOVERY AND USE OF WOOD ACETYLATION FLUID

(71) Applicant: Tricoya Technologies Ltd, London (GB)

(72) Inventors: Stephen John Benstead, London (GB); Benjamin Thomas Painter, London (GB)

(73) Assignee: Tricoya Technologies Ltd, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/327,043

(22) PCT Filed: Jul. 17, 2015

(86) PCT No.: PCT/EP2015/066449
§ 371 (c)(1),
(2) Date: Jan. 18, 2017

(87) PCT Pub. No.: WO2016/009060
PCT Pub. Date: Jan. 21, 2016

(65) Prior Publication Data
US 2017/0166509 A1  Jun. 15, 2017

(30) Foreign Application Priority Data
Jul. 18, 2014 (GB) .................................. 1412837.5

(51) Int. Cl.
*C07C 51/56* (2006.01)
*C07C 51/44* (2006.01)
*B27K 3/34* (2006.01)

(52) U.S. Cl.
CPC ................ *C07C 51/56* (2013.01); *B27K 3/34* (2013.01); *C07C 51/44* (2013.01); *B27K 3/346* (2013.01); *Y02P 20/582* (2015.11)

(58) Field of Classification Search
None
See application file for complete search history.

(56) References Cited

U.S. PATENT DOCUMENTS

| | | | | |
|---|---|---|---|---|
| 8,168,824 B2 * | 5/2012 | Warner | ................... | C07C 51/48 562/608 |
| 2004/0258941 A1 * | 12/2004 | Neogi | ....................... | C08B 3/00 428/537.1 |
| 2014/0066653 A1 | 3/2014 | Warner et al. | | |

FOREIGN PATENT DOCUMENTS

| | | |
|---|---|---|
| CN | 203092692 U | 7/2013 |
| EP | 0213252 | 3/1987 |
| EP | 0680810 | 11/1995 |

OTHER PUBLICATIONS

Climate Change and China Forestry Carbon Sequestration (with translation).
Basic Principles of Organic Chemistry (with translation).

* cited by examiner

*Primary Examiner* — Ana Z Muresan
(74) *Attorney, Agent, or Firm* — OspreyIP, pllc; James R. Cartiglia

(57) ABSTRACT

Disclosed is the integration of the production of acetic anhydride from ketene, and the acetylation of wood using acetylation fluid comprising acetic acid and acetic anhydride. The invention involves recirculating acetylation fluid recovered from wood acetylation to a unit for the production of acetic anhydride from acetic acid and ketene. The acetic anhydride product stream can, in turn, be directly used as a wood acetylation fluid.

7 Claims, 2 Drawing Sheets

RECOVERY AND USE OF WOOD ACETYLATION FLUID

FIELD OF THE INVENTION

The invention pertains to a process for the recovery of acetylation fluid from a wood acetylation process. Particularly, the invention pertains to a process for the integration of the acetylation of wood and the production of acetic anhydride from acetic acid, and an integrated plant.

BACKGROUND OF THE INVENTION

A well-known process for the production of acetic anhydride from acetic acid involves the formation of ketene (ethenone). Thereby ketene is produced by dehydrating acetic acid at high temperatures (typically in a ketene furnace operated at temperatures of the order of 700° C. to 750° C.). Subsequently, the ketene is reacted with acetic acid in an exothermic reaction leading to the formation of acetic anhydride.

Interestingly, both acetic acid and acetic anhydride are used in processes for the acetylation of wood. These processes, for which there is an increasing demand, serve to provide the wood with improved material properties, e.g. dimensional stability, hardness, durability, etc. In these processes, excess acetylation medium, typically a mixture of acetic anhydride and acetic acid, is ultimately removed from the wood. It is thereby desired to avoid wasting the removed acetylation medium, and preferably to recirculate and re-use it in wood acetylation.

Suitable techniques exist for recovering acetic anhydride, by separating it from acetic acid, after which the acetic anhydride can be re-used in wood acetylation. The acetic acid, however, comes in an excess ratio after wood acetylation as it is formed as a byproduct thereof, and it would be desired to put this to separate use, sell it as a chemical, and/or use it in the production of ketene. However, the specific source of the acetic acid, viz. from the acetylation of wood, comes with inherent limitations to their further use due to the presence impurities such as that of terpenes and terpenoid impurities from the wood. Particularly terpenes and terpenoids are difficult to remove. This limits the use of acetic acid as recovered from wood acetylation. E.g., using it in a ketene furnace is not desired, as the aforementioned impurities are prone to result in coke formation in the furnace, as a result of the high temperatures applied therein.

The foregoing issue is addressed in WO 2009/120257, by azeotropic distillation, wherein acetic acid comprising the aforementioned impurities is supplied to a distillation column together with water. Whilst the reference thus teaches a method of obtaining purified acetic acid from wood acetylation, it does not relate to the production of acetic anhydride and, particularly, it does not teach how to effectively integrate the production of acetic anhydride and the acetylation of wood. Also, the addition of water to the distillation column reduces the economic feasibility of the process.

It is desired to provide a method by which the acetylation of wood and the production of acetic anhydride can be effectively integrated. Also, it is desired to thereby make optimal use of sources of liquid as available from wood acetylation.

SUMMARY OF THE INVENTION

In order to better address one or more of the foregoing desires, the invention, in one aspect, concerns a process for the recovery of acetylation fluid from a wood acetylation process, said fluid comprising acetic acid and acetic anhydride, wherein the fluid is used as a reactant feed to a unit for the production of acetic anhydride from ketene and acetic acid, wherein the ketene is supplied to said unit as a reactant feed.

In a further aspect, the invention provides a system comprising a wood acetylation plant and an acetic anhydride production plant, wherein the acetic anhydride production plant comprises a unit for the production of ketene from acetic acid and, downstream thereof, a unit for the production of acetic anhydride from ketene and acetic acid and wherein the wood acetylation plant comprises a wood acetylation unit comprising an inlet and an outlet for acetylation fluid, wherein the outlet for acetylation fluid is in fluid communication with an inlet for acetic acid in the unit for the production of acetic anhydride.

DETAILED DESCRIPTION OF THE INVENTION

Figure 1:
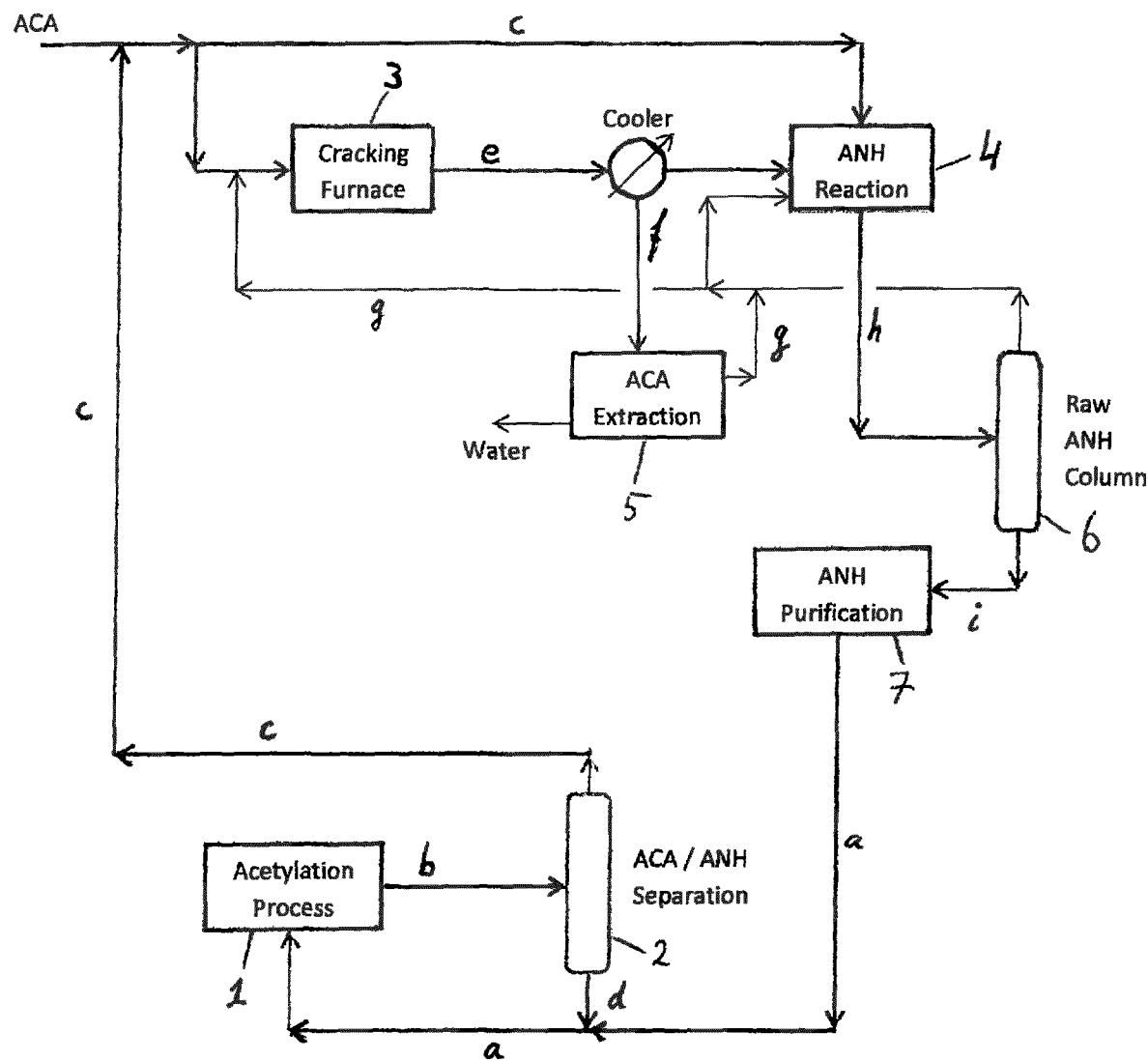
FIG. 1 shows a scheme for a wood acetylation plant coupled to an acetic anhydride production plant without additional measures, not according to the invention.

In a broad sense, the invention is based on the judicious insight that acetylation fluid as recovered from wood acetylation, even though comprising terpenes and/or terpenoids, can be submitted (preferably after filtering it from wood residues) to a unit producing acetic anhydride from acetic acid and ketene, to which the ketene is supplied as a reactant feed. The recovered acetylation fluid will then be a feed of acetic acid to said reactor. The fact that the fluid also contains acetic anhydride is not imperative. For, the reaction to produce acetic anhydride from ketene and acetic acid is not a delicate equilibrium that would be affected by the additional presence of acetic anhydride. By the judicious choice to combine a wood acetylation unit with an acetic anhydride production unit based on ketene conversion, it is thus possible to make good use of the acetic acid as recovered, by sending this to the acetic anhydride production unit rather than to the ketene production unit (ketene furnace).

The unit for the production of acetic anhydride receives, on one hand, the acetylation fluid from the wood acetylation process as a reactant feed and, on the other hand, ketene as another reactant feed. In a preferred embodiment, ketene is produced in a ketene production unit such as a cracking furnace, e.g. from fresh acetic acid.

In the event of sending the recovered acetylation fluid, which includes a substantial amount of acetic anhydride, to the acetic anhydride production section, it can be advisable to adjust the capacity of said section. The skilled person will be able to straightforwardly determine whether an existing acetic anhydride production section (e.g. a reaction vessel) has a sufficient capacity to handle the additional amount of fluid to be passed through it. Also, the skilled person will be aware how to enlarge the capacity of such a unit as necessary.

The acetic anhydride produced can be put to any use. However, in accordance with the invention it is preferred to provide a fully integrated process, wherein the formed acetic anhydride is recirculated to the feed stream of acetylation fluid, used in a unit for the acetylation of wood, preferably the same unit from which the acetylation fluid is recovered as discussed above.

Thus, in a preferred embodiment of the invention, an integrated process results wherein acetylation fluid recovered from wood acetylation is re-used as a feed to a unit for the production of acetic anhydride, and the product stream thereof is sent back to the wood acetylation. This product stream, which comprises acetic anhydride (as produced and as originally present) and acetic acid can itself be used as an acetylation fluid.

Conventionally, the output of the acetic anhydride production unit would require adjustment of the ratio of acetic anhydride to acetic acid, so as to become richer in acetic anhydride. This is related to the fact that a full conversion of acetic acid into acetic anhydride will usually not be achieved in practice. A unit for the separation of acetic acid and acetic anhydride (typically a distillation column, sometimes referred to as a "raw anhydride column") can then be employed in order to adjust the ratio of acetic anhydride to acetic acid in the product stream coming from the acetic anhydride production unit. The output of said separation unit will preferably be suitable for as a wood acetylation fluid, such fluid preferably comprising acetic anhydride (ANH) and acetic acid (ACA) in a ratio ANH:ACA of from 80:20 to 100:0, preferably 90:10 to 95:5.

In carrying out the invention such a separation unit can be included. However, in view of the presence of acetic anhydride in the recovered acetylation fluid that is recirculated to a unit in which acetic acid and ketene are reacted to form acetic anhydride, the product stream obtained from this unit will be richer in acetic anhydride than in a conventional situation, without the recirculation of acetylation fluid. Thus, the judicious recirculation scheme of the invention allows dispensing with the aforementioned "raw anhydride column". This is an advantage, leading to reduced equipment and operational costs.

The integration of wood acetylation and acetic anhydride production according to the invention can be carried out both in existing plants and in designing new plants. E.g., a new ketene-based production unit for acetic anhydride can be built next to an existing wood acetylation unit, and coupled to it in accordance with one or more embodiments of the invention. Also, a new wood acetylation unit can be built next to an existing ketene-based production unit for acetic anhydride. Or, in the event that a wood acetylation unit and a ketene-based acetic anhydride production unit already exist next to each other, these can become integrated. In the event that the units are already integrated in another way, the manner in which such plants are coupled can be changed so as to be in conformity with the invention as described hereinbefore.

The equipments and technologies applied are well-known to the skilled person. This pertains to units for the acetylation of wood, such as wood acetylation reactors, and the customary ancillary equipment thereof, e.g. a filter section for removing wood residues from recovered acetylation fluid. Similarly, this pertains to distillation units (distillation equipment such as a distillation column), to ketene production sections (typically a ketene furnace), acetic anhydride production sections (typically a reactor suitable for reacting ketene with acetic acid).

Wood acetylation units for use in the present invention can be those suitable for the acetylation of solid wood, such as wood beams or planks. Said wood acetylation units can also be those suitable for the acetylation of wood elements such as flour, fibres, strands, or chips. The wood acetylation processes applied in the present invention thus are not limited to any size, shape, or species of wood. A great variety of such processes is well-known to the skilled person.

The invention also pertains to a system comprising a wood acetylation plant integrated with an acetic anhydride production plant. Therein the acetic anhydride production plant comprises a unit for the production of ketene from acetic acid and, downstream thereof, a unit for the production of acetic anhydride from ketene and acetic acid. The wood acetylation plant comprises an acetylation unit, typically a reactor, comprising an inlet and an outlet for acetylation fluid. The outlet for acetylation fluid, i.e. as recovered after wood acetylation, is in fluid communication with an inlet for acetic acid in the acetic anhydride production unit. The latter unit has an outlet for produced acetic anhydride, which is in fluid communication, directly or indirectly, with an inlet for acetylation fluid in the wood acetylation unit. In the event of this communication being indirectly, this is typically the case if a separation unit, such as a distillation column, is placed between the anhydride production section and the wood acetylation unit.

The invention will be further explained hereinafter with reference to the drawings. These drawings do not limit the invention. As the drawings may relate to specific embodiments of the invention, the skilled person will understand that the invention is more generally applicable, and the disclosure in the drawings is not limited to any specific designs or numbers given therein.

In the figures, the following elements are shown.

Equipment Parts:
(1) Wood acetylation plant
(2) Acetic acid/acetic anhydride separation unit
(3) Ketene production unit
(4) Acetic anhydride production unit
(5) Treatment section for recovering residual aqueous acetic acid
(6) Acetic anhydride distillation unit
(7) Acetic anhydride purification unit Process Streams:
(a) Fresh acetylation fluid
(b) Acetylation fluid recovered from wood acetylation
(c) Acetic acid
(d) Acetic anhydride separated from acetic acid
(e) Ketene
(f) Residual aqueous acetic acid
(g) Acetic acid recovered
(h) Raw acetic anhydride (mixture with acetic acid)
(i) Enriched acetic anhydride (reduced acetic acid content)

FIG. 1 shows a scheme for a ketene-based acetic anhydride production plant (comprising a ketene production unit (3) and an acetic anhydride production unit (4) integrated with a wood acetylation plant (1). Herein the plants are coupled without any additional measures, i.e. not according to the invention. Acetylation fluid (stream a) is fed to a wood acetylation plant (1). Recovered acetylation fluid (b) is subjected to acetic acid separation in a first acetic acid/acetic anhydride separation unit (2), resulting in a stream (c) of acetic acid separated from acetic anhydride and a stream (d) of acetic anhydride separated from acetic acid. The stream (c) of acetic acid separated from acetic anhydride is sent to an acetic anhydride production section comprising a ketene production unit (3) and an acetic anhydride production unit (4). The ketene production unit (3) is connected to, downstream thereof, a treatment section (5) for recovering residual aqueous acetic acid (f). Acetic acid recovered therefrom (g) is sent to the ketene production unit (3) and/or the acetic anhydride production unit (4). Ketene produced (e) is sent to an acetic anhydride production unit (4). Raw anhydride produced (h) is sent to an acetic anhydride distillation unit (6). Acetic acid obtained therefrom (c) is sent to the acetic anhydride production section mentioned above. The enriched acetic anhydride (i), having a reduced acetic acid content, is sent to a purification unit (7) and purified acetylation fluid thereby obtained (i) is fed, as fresh acetylation fluid (a) to the wood acetylation section (1).

Figure 2:
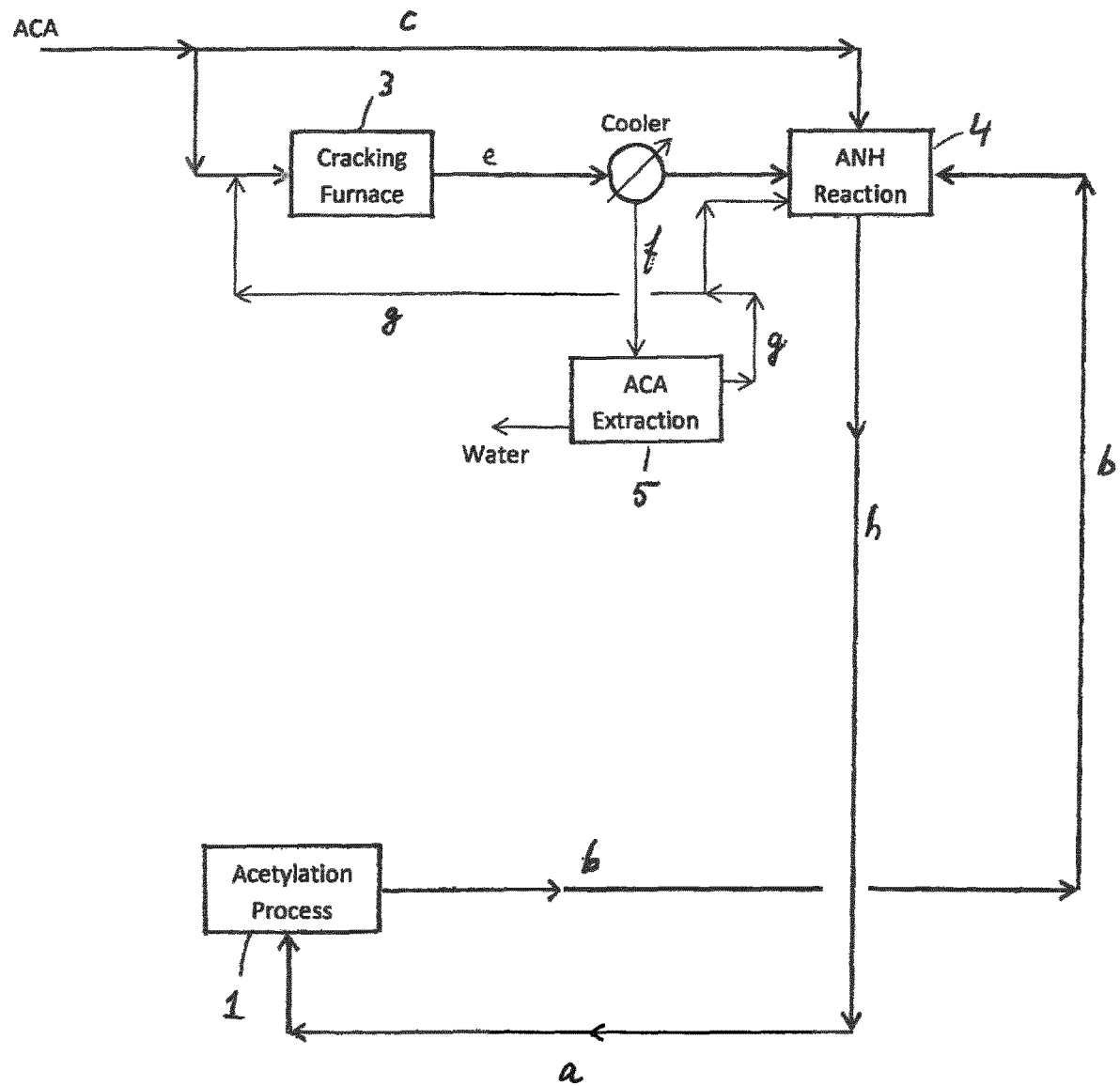
FIG. 2 shows a scheme for a wood acetylation plant coupled to an acetic anhydride production plant according to an embodiment of the invention.

FIG. 2 shows a scheme for a ketene-based acetic anhydride production plant integrated with a wood acetylation plant in accordance with an embodiment of the invention. Herein the stream (b) of acetylation fluid recovered from wood acetylation is sent to the acetic anhydride production unit (4). The acetic anhydride product stream (h) is sent to the wood acetylation section (1), and thereby directly used as wood acetylation fluid (a).

It will be understood that the schematic drawings serve to illustrate some parts of the equipments and production units as necessary to further illustrate some embodiments of the invention. The skilled person will be well aware of equipment parts and flow lines now shown, such as devices for providing heat, devices for providing pressure, vents for off-gas, and so on.

Where, in this description, it is spoken of "fluid communication", this refers to any connection between a first part or section of a plant and a second part or section of a plant via which fluids, including liquids and gases, can flow from the first part of the plant to the second part of the plant. In the event of liquids, such fluid communication is typically provided by piping systems, hoses, or other devices well-known to the skilled person for the transportation of fluids. In the event of gases, such fluid communication is typically provided by gas flow lines. Such gas flow lines typically comprise piping systems, or other devices well-known to the skilled person for the transportation of gases, if needed under pressures that are above atmospheric pressures or below (vacuum).

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein described units, such as a wood acetylation unit, a reactor unit or a distillation unit, comprise a plurality of such units positioned in parallel or in series.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

The invention claimed is:

1. A process for the production of acetic anhydride comprising supplying a ketene reactant feed and an acetic acid reactant feed to a unit producing acetic anhydride from ketene and acetic acid, wherein the acetic acid reactant feed is acetylation fluid which is recovered from a wood acetylation process and which contains acetic acid and acetic anhydride and is send directly to the unit for production of acetic anhydride.

2. The process according to claim 1, wherein the acetic acid reactant feed as supplied into said unit comprises terpenes and/or terpenoids.

3. The process according to claim 1, wherein the ratio of acetic anhydride to acetic acid in the product stream coming from said unit is not adjusted using a distillation column.

4. The process according to claim 1, wherein fluid resulting from said unit is recirculated as an acetylation fluid to said wood acetylation process.

5. The process according to claim 1, further comprising producing ketene in a ketene production unit from acetic acid and supplying produced ketene to said unit wherein acetic anhydride is produced from ketene and acetic acid.

6. The process according to claim 1, wherein the process is an integrated process comprising:
    acetylating wood,
    obtaining acetylation fluid from the wood acetylation,
    re-using said acetylation fluid as reactant feed in a unit for the production of acetic anhydride from ketene and acetic acid,
    providing a ketene reactant feed to said unit, and
    using the product stream comprising acetic anhydride and acetic acid from said unit as an acetylation fluid in said wood acetylation.

7. The process according to claim 1, wherein the process comprises:
    recovering acetylation fluid from a wood acetylation process,
    sending the recovered acetylation fluid, which includes an amount of acetic anhydride, to said unit,
    and producing in said unit acetic anhydride by reacting acetic acid, which is also included said recovered acetylation fluid, with ketene.

* * * * *